United States Patent
Cohen et al.

(10) Patent No.: US 10,064,886 B2
(45) Date of Patent: Sep. 4, 2018

(54) COMPOSITION BASED ON XYLOGLUCAN AND PROTEINS FOR THE TREATMENT OF INTESTINAL DISORDERS

(71) Applicant: NOVINTETHICAL PHARMA SA, Pambio Noranco, Lugano (CH)

(72) Inventors: Miguel Angel Alonso Cohen, Barcelona (ES); Michele Giuseppe Di Schiena, Robecco Sul Naviglio (IT); Marco Di Fulvio, Lugano (CH)

(73) Assignee: NOVINTETHICAL PHARMA SA, Pambio Noranco (CH)

( * ) Notice: Subject to any disclaimer, the term of this patent is extended or adjusted under 35 U.S.C. 154(b) by 0 days.

(21) Appl. No.: 15/597,664

(22) Filed: May 17, 2017

(65) Prior Publication Data

US 2017/0252366 A1   Sep. 7, 2017

Related U.S. Application Data

(63) Continuation of application No. 15/303,753, filed as application No. PCT/EP2015/058162 on Apr. 15, 2015.

(30) Foreign Application Priority Data

Apr. 15, 2014 (IT) .............................. MI2014A0705

(51) Int. Cl.

| A61K 31/716 | (2006.01) |
| A61K 47/36 | (2006.01) |
| A61K 47/42 | (2017.01) |
| A61K 31/00 | (2006.01) |
| A61K 45/06 | (2006.01) |
| A61K 38/01 | (2006.01) |
| A61K 9/00 | (2006.01) |

(52) U.S. Cl.
CPC .......... *A61K 31/716* (2013.01); *A61K 9/0078* (2013.01); *A61K 31/00* (2013.01); *A61K 38/01* (2013.01); *A61K 45/06* (2013.01); *A61K 47/36* (2013.01); *A61K 47/42* (2013.01)

(58) Field of Classification Search
CPC ...... A61K 38/01; A61K 31/00; A61K 31/716; A61K 47/36; A61K 47/42; A61K 45/06; A61K 9/7008
USPC ............... 514/13.2, 17, 2, 21.2, 54
See application file for complete search history.

(56) References Cited

U.S. PATENT DOCUMENTS

| 3,515,667 A | 6/1970 | Mogg |
| 4,070,488 A | 1/1978 | Davis |
| 4,334,886 A | 6/1982 | Tani et al. |
| 4,783,446 A | 11/1988 | Neushul |
| 5,262,315 A | 11/1993 | Gross et al. |
| 5,444,054 A * | 8/1995 | Garleb ................... A23L 33/12 426/72 |
| 6,203,797 B1 | 3/2001 | Perry |
| 6,387,210 B1 | 5/2002 | Hsu et al. |
| 6,811,243 B2 | 11/2004 | Pearlstine et al. |
| 7,371,776 B2 | 5/2008 | Ramljak et al. |
| 7,435,432 B2 | 10/2008 | Olson |
| 2010/0129335 A1* | 5/2010 | Rochat ................ A61K 35/745 424/93.45 |

FOREIGN PATENT DOCUMENTS

| EP | 2526939 A1 | 11/2012 | |
| WO | 2006131262 A1 | 12/2006 | |
| WO | WO 2006/131262 A1 * | 12/2006 | ............... A61K 9/00 |
| WO | 2009008005 A1 | 1/2009 | |
| WO | 2014020408 A1 | 2/2014 | |

OTHER PUBLICATIONS

The Merck Manual, 1992, pp. 834-845.*
Mishra et al, J. Mater. Chem. 2009, 19, 8528-8536.*
Bueno L., "Xyloglucan: a new agent to protect the intestinal mucosa and to prevent bacterially-mediated alteration of tight junction permeability," Oct. 22, 2014 UEG Week Vienna 2014.
Final Office Action cited in U.S, Appl. No. 14/566,546.
Havinga R., et al., "*Tamarindus indica* L. (*Fabaceae*): Patterns of use in traditional african medicine", Journal of Ethnopharmacology, vol. 127, No. 3, Feb. 17, 2010, pp. 573-588.
Huang Y., et al., "Water-insoluble fiber-rich fraction from pineapple peel improves intestinal function in hamsters: evidence from cecal and fecal indicators", Nutrition Research, vol. 34, No. 4 Mar. 12, 2014, pp. 346-354.
International Preliminary Report on Patentability of PCT/EP2015/158162 dated Jul. 13, 2016.
Kiyoshi, E., et al., "Comparative effect of water-soluble and -insoluble dietary fiber on bowel function in rats fed a liquid elemental diet", Jan. 1, 1998, p. 883491.
Merck Manual, 1992, pp. 834-845.
Mishra A., et al., "Tamarind xyloglucan: a polysaccharide with versatile application potential," J. Mater Chem. 2009, 19, 8528-8536.
Nie, W., et al., "Tamarind seed xyloglucans promote proliferation and migration of human skin cells through internalization via stimulation of proliferative signal transduction pathways," Dermatology Research and Practice, vol. 35, No. 5-6, Jan. 1, 2013, pp. 455-514.
Search Report and Written Opinion of PCT/EP2015/058162 dated Jun. 16, 2015.

* cited by examiner

*Primary Examiner* — Ganapathy Krishnan
(74) *Attorney, Agent, or Firm* — Silvia Salvadori, P.C.; Silvia Salvadori

(57) ABSTRACT

Disclosed are compositions comprising synergic combinations of xyloglucans and plant or animal proteins, which are useful in the treatment of intestinal disorders.

6 Claims, 1 Drawing Sheet

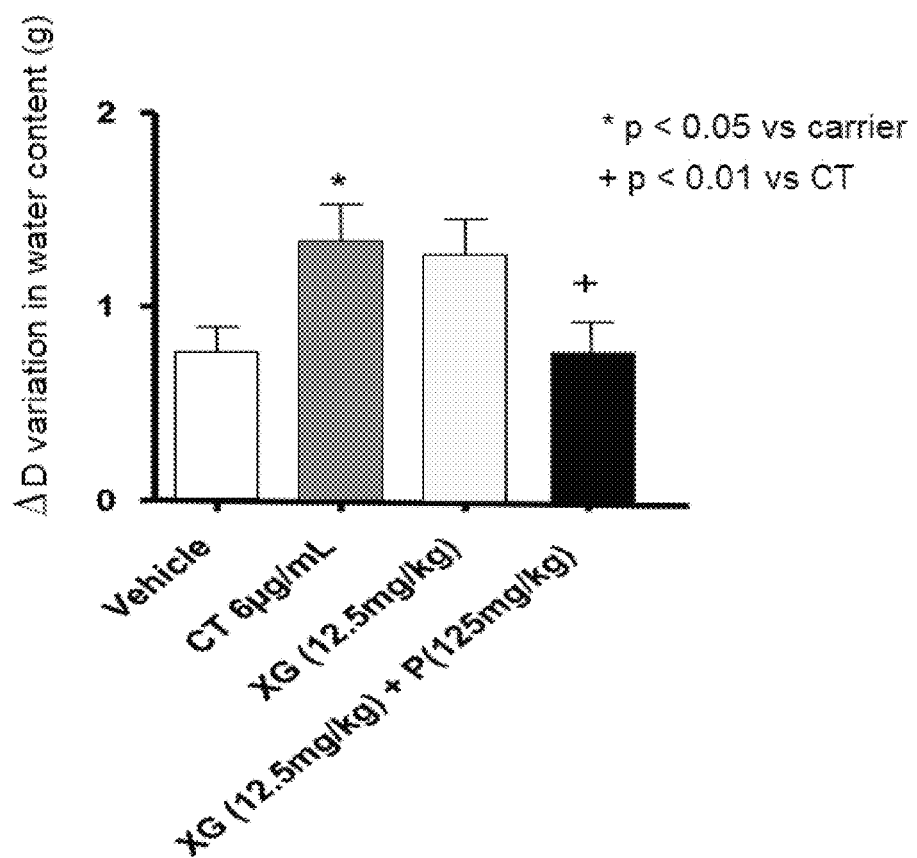

COMPOSITION BASED ON XYLOGLUCAN AND PROTEINS FOR THE TREATMENT OF INTESTINAL DISORDERS

This Non-Provisional Application is a continuation of U.S. Ser. No. 15/303,753, filed on Oct. 13, 2016, which is a U.S. National Stage of PCT/EP2015/058162 filed on 15 Apr. 2015, which claims priority to and the benefit of Italian Application No. MI2014A000705 filed on 15 Apr. 2014, the contents of which are incorporated herein by reference in their entireties.

The invention relates to synergic combinations of xyloglucans and plant or animal proteins and compositions for the treatment of intestinal disorders, especially diarrhoeal forms of various origins.

PRIOR ART

Diarrhoea is a symptom of many gastrointestinal disorders and is often incapacitating and dangerous, especially in children and the elderly. Acute diarrhoea is mainly caused by intestinal infections, but can also be due to the use of medicaments or radiotherapy and to other pathological conditions (diverticulitis, heavy-metal poisoning, intestinal ischaemia, allergies and intolerances).

Acute diarrhoea with an infectious cause is a serious problem in developing countries; it is believed to cause the death of at least 4 million children under 5 years old every year.

Chronic diarrhoea is generally due to irritable bowel syndrome, coeliac disease or inflammatory bowel diseases (Crohn's disease, ulcerative rectocolitis).

In view of their different aetiologies, various treatment options are available, based on the administration of antibiotics/antibacterials, spasmolytics/anticholinergics, probiotics, or opioid receptor agonists. However, some of said treatments must be administered with great caution, because they do not act on the causal pathological process.

To prevent said adverse effects, complexes of tannins complexed with animal proteins and gelatins, in particular with gelatin of bovine origin, albumin, casein or ovalbumin, have been proposed for some time.

For example, the use of said complexes in the treatment of the various forms of diarrhoea is disclosed in EP 1764105, EP 2526939, EP 2361623 and US 20090062191. Gelatin tannate has been available on the market for some time as a medical device for the treatment of acute diarrhoea.

Xyloglucans are molecules consisting of a linear backbone of β-1,4-glucans with short side branches. The latter bond due to the xylose bonded to oxygen in the 6 position of the sugar. Said side chains can also contain other sugars such as arabinose and fucose.

Xyloglucans belong to the hemicellulose family, which combines with cellulose in the cell wall of the higher plants. A particularly rich source of xyloglucan is the seeds of tamarind (*Tamarindus indica*), a tropical tree originating from East Africa.

Xyloglucan-rich tamarind seed extracts are known and have been used in the medical field mainly as viscosity-controlling agents in ophthalmic compositions (U.S. Pat. No. 6,056,950), as mucoadhesive agents (WO 2006131262), as artificial tears (WO 2009/044423), as anti-infective agents (WO 2011147767) and as anti-inflammatory agents (WO 2011147768).

BRIEF DESCRIPTION OF THE DRAWINGS

FIG. 1 shows that xyloglucan alone did not reduce the fluid secretion.

DESCRIPTION OF THE INVENTION

It has now surprisingly been found that combinations of xyloglucans with plant or animal proteins compatible with oral administration to humans are particularly effective in the treatment and prevention of diarrhoea and other infectious and/or inflammatory intestinal disorders. Xyloglucans exert a film-forming effect in the intestinal mucosa which reduces the permeability of the tight junctions of the intestinal mucosa, and therefore prevents the entry of the pathogens responsible for acute intestinal infections. The film-forming effect is not affected by variations in pH.

The invention therefore relates to pharmaceutical compositions comprising, as active ingredients, xyloglucans or extracts containing them, combined with at least one plant or animal protein selected from gelatine, albumin, ovalbumin, casein, pea protein and soya protein and suitable excipients, and optionally with other active ingredients useful for the prevention and treatment of gastrointestinal and urogenital disorders.

Xyloglucans extracted from *Tamarindus indica* are available on the market, for example from Indena (Italy) (Xilogel®) and DSP Gokyo Food & Chemical (Japan) (Glyloid®). The average molecular weight is between 400,000 and 650,000 daltons.

Preferred proteins include gelatin and pea protein. Gelatin is particularly preferred.

The weight ratio of xyloglucan to protein ranges between 1:0.5 and 1:30. The combination of xyloglucan and protein forming the subject of the invention constitutes the active ingredient of oral pharmaceutical formulations.

Examples of suitable forms of administration include capsules, tablets, solutions, suspensions, granules, gels and the like.

Other active ingredients with which xyloglucans and protein can be combined include antibiotics, antimotility agents, steroidal and non-steroidal anti-inflammatories, compounds for the treatment of gastrointestinal bloating (simethicone and the like), mesalazine, sucralfate, natural and synthetic polysaccharides such as pectins, chitosan (animal or vegetable), hyaluronic acid, guar gum, xanthan gum, cellulose and hemicellulose and derivatives such as hydroxypropylcellulose, carrageenans, carbomers, and crosslinking/polymerising compounds such as ferulic acid; polyphenols, such as gall polyphenols, polyphenols from grape pips, probiotics such as Lactobacilli, Bifidobacteria, yeasts and the like.

In the compositions according to the invention, xyloglucans can be present in a wide concentration range which depends on the type of composition and the therapeutic indication for which they are intended.

The xyloglucan is administered orally at doses ranging between 0.5 mg/dose and 200 mg/dose, preferably between 10 mg/dose and 100 mg/dose. The protein, in particular gelatin, is administered orally at doses ranging between 10 mg/dose and 3000 mg/dose, preferably between 50 mg/dose and 500 mg/dose.

The compositions according to the invention are useful for the treatment and prevention of gastrointestinal disorders and other disorders that originate in the gastrointestinal system and are transferred to other systems, such as the urogenital system. It is known that the Gram-negative bacteria present in the intestine, in particular *Escherichia coli*, can proliferate in said organ and migrate to the urinary tract, where they cause 90% of urogenital infections such as cystitis, cystopyelitis and the like.

In particular, the compositions according to the invention are useful to prevent the proliferation of pathogens in the gastrointestinal system and transfer them to other systems of the human body through the tight intestinal junctions, to protect the intestinal mucosa against chemical or physical agents which can reduce the functionality and natural regeneration of the intestinal epithelium, and to reduce the paracellular flow of pathogens through the intestinal walls.

The compositions according to the invention have also proved useful for the prevention and treatment of damage to the intestinal mucosa and the consequent inflammatory symptoms, such as diverticulosis and the early stages of diverticulitis; for the treatment of symptoms resulting from food allergies (e.g. intolerance of lactose, gluten, etc.); for the prevention and treatment of digestive disorders (gas production, bloating, stomach rumble and flatulence); and for the prevention and treatment of damage to the intestinal mucosa deriving from local inflammatory phenomena of transient or chronic origin, in particular for the treatment of Crohn's disease, ulcerative colitis and irritable bowel syndrome (IBS).

The compositions according to the invention can be advantageously used to treat diarrhoea in combination with oral rehydration electrolytes, such as mucomimetics, and to inhibit the adherence of bacteria to the mucosa and subsequent proliferation involving dysbiosis, optionally combined with probiotics or tyndallised bacteria. The compositions according to the invention are useful for the prevention and treatment of travellers' diarrhoea.

The compositions according to the invention effectively protect the mucosa and reduce the adherence to it of some pathogens, such as gas-producing bacteria.

The examples below illustrate the invention in greater detail.

EXAMPLE 1

Composition for the Prevention and Treatment of Diarrhoea; Single-dose Sachet

| | |
|---|---|
| Xyloglucan | 0.100 g |
| Gelatin | 0.050 g |
| Inulin | 1.650 g |
| Maltodextrin | 1.195 g |
| Stevioside (Stevia) | 0.015 g |
| Tuttifrutti flavouring (Firmenich) | 0.015 g |
| E160 (a) colouring (betacarotene) | 0.025 g |

EXAMPLE 2

Composition for the Prevention and Treatment of Diarrhoea; Hard Capsule

| | |
|---|---|
| Xyloglucan | 0.1 g |
| Gelatin | 3.0 g |
| Matricaria E.S. | 0.026 g |
| Pectin | 0.050 g |
| Dimethicone | 0.020 g |
| Kaolin | 0.020 g |
| Magnesium stearate | 0.080 g |

EXAMPLE 3

Composition for the Prevention and Treatment of Diarrhoea; Tablet

| | |
|---|---|
| Xyloglucan | 0.1 g |
| Pea protein | 0.5 g |
| Lactose | 0.063 g |
| Anhydrous colloidal silicon dioxide | 0.002 g |
| Microcrystalline cellulose | 0.030 g |
| Magnesium stearate | 0.003 g |

EXAMPLE 4

Bioassays: Protection Against Intestinal Fluid Secretion Induced by Cholera Toxin in Rats Four groups of Wistar rats (200-220 g) were treated orally with 12.5 mg/kg of xyloglucan, 125 mg/kg of gelatin and the combination of said two ingredients of the combination, at the same dose. Six hours after administration, the groups of animals were treated with cholera toxin at the dose of 6 µg/ml.

Two hours after the toxin treatment the water content of the intestinal loop was measured.

The results obtained, shown in the FIG. 1 and in the following Table, demonstrate that xyloglucan alone did not reduce the fluid secretion. Equally, gelatin alone did not exhibit a significant effect, whereas the effects of the combination proved statistically significant.

| | Basal[1] | Saline + CT[2] | 125 mg gelatine/kg/PO[3] - 6 hours | 12.5 mg xyloglucan/kg/PO[7] - 6 hours | 12.5 mg xyloglucan/kg/PO[5] + Gelatin (125 mg/kg)[6] - 6 hours | 12.5 mg xyloglucan/kg/PO[5] + Gelatin (250 mg/kg)[6] - 12 hours |
|---|---|---|---|---|---|---|
| Grams/loop p | 0.41 ± 0.11 | 1.04 ± 0.32 NS[4] | 1.01 ± 0.39 NS[4] | 1.26 ± 0.18 NS | 0.77 ± 0.15 Significant (p < 0.01) | 0.75 ± 0.16 Significant (p < 0.05) |

EXAMPLE 5

Clinical Trial

A multicentre controlled parallel-group clinical trial was conducted by administering to patients suffering from acute diarrhoea the combination according to the invention (xyloglucan 400 mg/day and gelatin 200 mg/day), the probiotic *S. boulardii* (at the dose of $7 \times 10^9$ cells/dose), and diosmectite (Smecta®, 3×3 g sachets/day). The speed of onset of clinical efficacy was evaluated in the three groups (reduction in duration of acute diarrhoea and the correlated symptoms). The symptoms examined were nausea, vomiting, flatulence, abdominal pain and stool emissions. The symptoms declined in all three groups. The combination according to the invention led to more rapid action, inhibiting the diarrhoea within 24 hours of the start of the treatment. Abdominal pain was monitored throughout the treatment. The patients did not present vomiting after 48 and 72 hours. The combination according to the invention gave rise to a more rapid reduction in stool emissions rated as grades 6 and 7 on the Bristol scale, with a 60% reduction as against 34% and 39% respectively for diosmectite and *S. boulardii*. After 48 hours this type of emission had almost entirely disappeared in all three groups. The combination according to the invention therefore proved to be the fastest-acting in preventing stool emissions.

The invention claimed is:

1. A Method of treating diarrhoea, Crohn's disease, ulcerative colitis and irritable bowel syndrome (IBS), diverticulosis, the early stages of diverticulitis, coeliac disease, lactose intolerance, cystitis and cystopyelitis in humans in need thereof, said method comprising administering to said humans an effective amount of a combination of xyloglucans or extracts containing them and gelatine.

2. The method according to claim 1, wherein the weight ratio between xyloglucan and gelatin is between 1:0.5 and 1:30.

3. The method according to claim 1 further comprising excipients.

4. The method according to claim 3 further comprising active ingredients selected from the group consisting of antibiotics, antimotility agents, steroidal or non-steroidal anti-inflammatories, compounds for the treatment of gastrointestinal bloating, natural or synthetic polysaccharides, and electrolytes.

5. The method according to claim 1, wherein said effective amount comprises between 0.5 mg/dose to 200 mg/dose xyloglucan and between 10 mg/dose to 3000 mg/dose gelatine.

6. The method according to claim 4, wherein said non-steroidal anti-inflammatories agents and said natural polysaccharides are selected from the group consisting of mesalazine, sucralfate, hyaluronic acid, guar gum, xanthan gum, cellulose and hemicellulose, hydroxypropyl cellulose, carrageenans, carbomers, ferulic acid; polyphenols and probiotics.

* * * * *